United States Patent
Ward

(10) Patent No.: US 7,037,336 B2
(45) Date of Patent: May 2, 2006

(54) MACULAR AND SCLERAL SUPPORT SURGICAL DEVICE FOR OCULAR RESTRAINT IN PROGRESSIVE HIGH MYOPIA

(76) Inventor: Brian Ward, 291 Quinnhill Ave., Los Altos, CA (US) 94024

( * ) Notice: Subject to any disclaimer, the term of this patent is extended or adjusted under 35 U.S.C. 154(b) by 171 days.

(21) Appl. No.: 10/463,474

(22) Filed: Jun. 16, 2003

(65) Prior Publication Data

US 2004/0254420 A1    Dec. 16, 2004

(51) Int. Cl.
*A61F 2/14*    (2006.01)
(52) U.S. Cl. .......................................... 623/4.1; 602/41
(58) Field of Classification Search ................ 623/4.1, 623/6.64, 11.11, 14.13; 602/41, 60, 61
See application file for complete search history.

(56) References Cited

U.S. PATENT DOCUMENTS

| | | | |
|---|---|---|---|
| 4,549,529 A | * | 10/1985 | White .......................... 128/898 |
| 6,059,828 A | | 5/2000 | Peyman ....................... 623/4.1 |
| 6,117,170 A | | 9/2000 | Batdorf, Sr. .................... 623/4 |
| 6,126,687 A | | 10/2000 | Peyman ......................... 623/4 |
| 6,197,056 B1 | | 3/2001 | Schachar .................... 623/4.1 |
| 6,322,545 B1 | | 11/2001 | Schachar .................... 604/294 |

OTHER PUBLICATIONS

LIX Edward Jackson Memorial Lecture, "Pathologic Myopia: Where Are We Now?", Yasuo Tano, MD; 2002.

* cited by examiner

Primary Examiner—Corrine McDermott
Assistant Examiner—William H Matthews
(74) Attorney, Agent, or Firm—Robert O. Guillot; Intellectual Property Law Offices

(57) ABSTRACT

The present invention is a flexible ocular restraint band that includes a thin flexible material such as a surgical mesh fabric with flexible reinforced end portions. The device is positioned posterior to the eye globe and the reinforced ends are sutured to anterior portions of the scleral ring. Preferably, a side edge of the band is formed with a concave curved edge to be placed proximate the optical nerve without making contact or applying pressure to the optical nerve. When properly positioned the device prevents further axial elongation of the eye. In alternative embodiments the band may be formed as a generally linear strap, a three legged or "Y" shaped strap or a four legged "X" shaped strap.

27 Claims, 4 Drawing Sheets

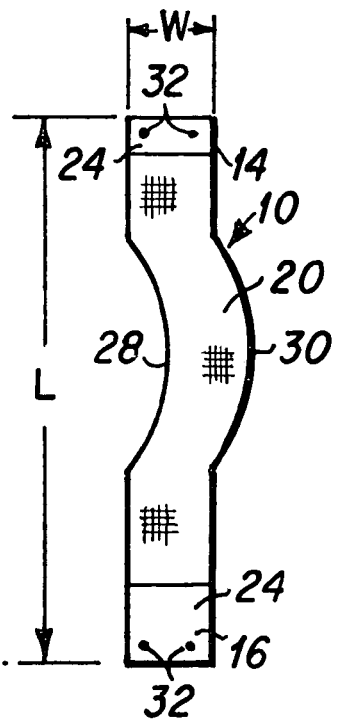
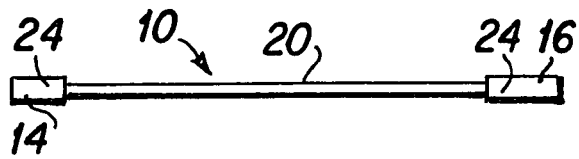
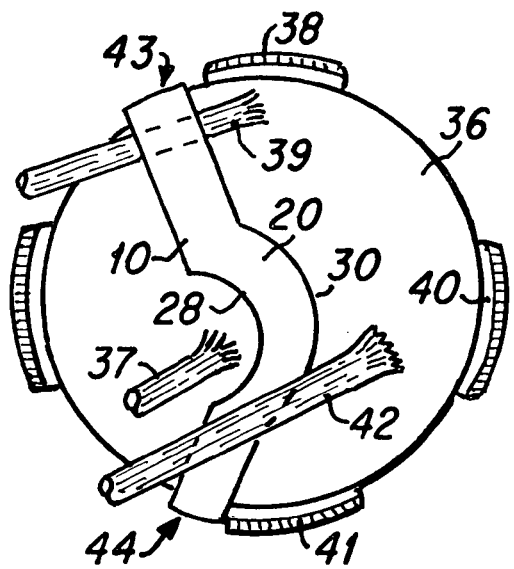
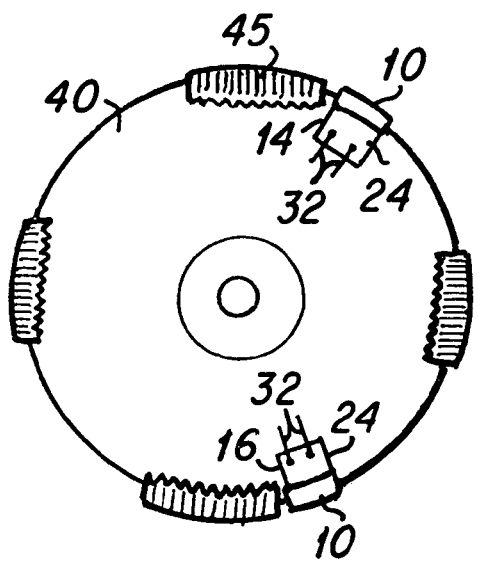
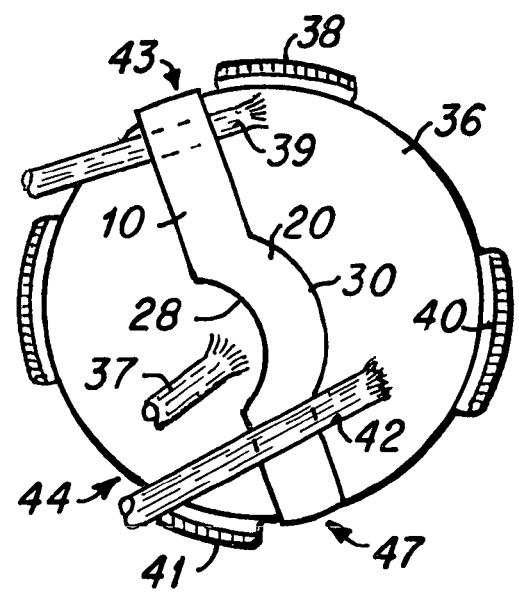

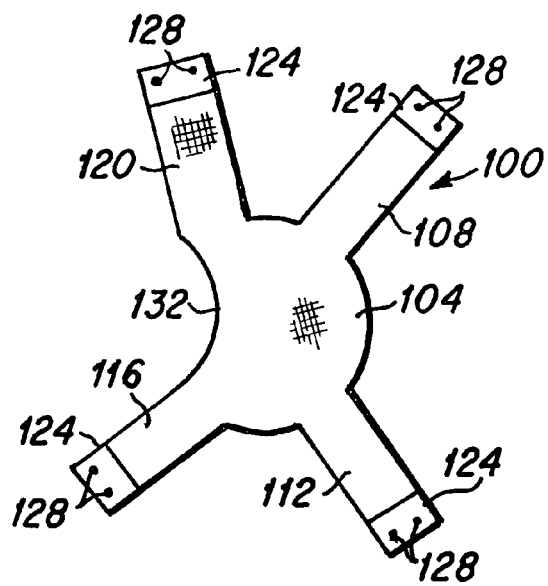
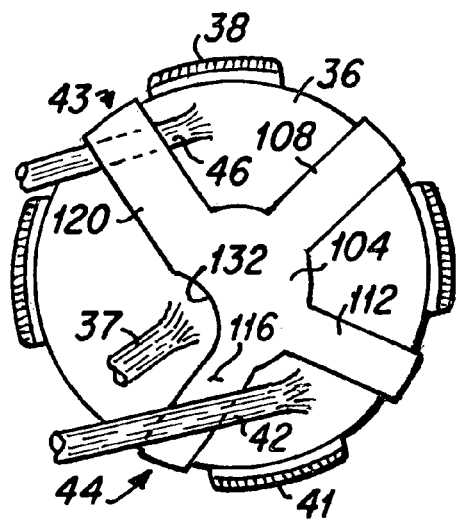
Fig.10          Fig.11
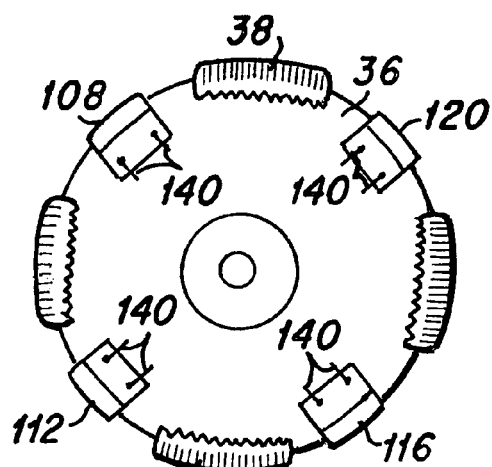
Fig.12

MACULAR AND SCLERAL SUPPORT SURGICAL DEVICE FOR OCULAR RESTRAINT IN PROGRESSIVE HIGH MYOPIA

FIELD OF THE INVENTION

The present invention relates generally to ocular support bands, and more particularly to a flexible band device for supporting the macular region of the eye.

BACKGROUND OF THE INVENTION

Degenerative myopia is a significant cause of world blindness and visual disability. It is said to be the seventh ranking cause of legal blindness in the United States of America, while being the fourth ranking cause in Hong Kong. Overall, blindness most commonly occurs from myopic macular degeneration, retinal detachment, cataract and glaucoma, and of these, myopic macular degeneration is the most important. There is no universally accepted treatment to prevent the condition. It is thought to be due to decompensation of the nerve and supporting tissues of the part of the retina of the eye, the macular, which is used for fine vision. One cause of the damage is the axial overgrowth of the eye during the regular growth phase, followed by further increments of stretching during the adult years. By middle age, stressed eye tissues begin to show degeneration and failure of function; crucially, this includes the delicate nerves of the retina.

A scleral reinforcement procedure has been employed for some 50 years in an attempt to prevent macular degeneration. The concept is to graft a strengthening layer of donor or autologous tissue over the weak scleral shell of the eye to reinforce it. This has been found to have limited success, especially in adult eyes. Surgical fabrics have been used in a few studies but with no accepted success. One example of a device of this type is taught in U.S. Pat. No. 6,126,687, issued Oct. 3, 2000 to Peyman. This patent teaches the use of a strip of mesh-like material to apply pressure to the posterior portion of the eye as a treatment for age-related macular degeneration. Many surgeons have found such mesh-like materials difficult to use, in that the suturing of the mesh fabric material creates gathering, folds, pulls and creases in the fabric that are problematic. Thus, surgeons have generally reverted to the use of bands of donor sclera for the reinforcement of the distensible scleral wall of the eye. These grafts take the form of a strip of donor sclera tissue placed over the posterior part of the eye and secured by sutures to the outer coat of the eye to be treated to retard growth and stretching.

Scleral buckling is a related common surgical technique used by ophthalmologists in the repair of retinal detachments. Buckles, made usually of silicone rubber, are sutured to the wall of the eye in such a way as to produce an indentation, so approximating the wall of the eye to an underlying detached retina.

SUMMARY OF THE INVENTION

To restrain the overgrowth and stretching of a selected eye, with pathological conditions, such as axial myopia, by the surgical application of a thin flexible restraint composed of manmade materials well accepted as being appropriate for long-term implantation in the human body and previously used in surgery of the eye and it's adnexa. The most numerous individuals for whom this treatment would be helpful are those with progressive stretching axial elongation which causes vision loss through severe damage to the various tissues of the eye.

Generally, the present invention is a flexible macular and scleral support device that includes a thin flexible material such as surgical mesh fabric with flexible reinforced end portions. The device is positioned posterior to the eye globe and the reinforced ends are sutured to anterior portions of the scleral ring. Preferably, a side edge of the band is formed with a concave curved edge to be placed proximate to the optic nerve without making contact or applying pressure to the nerve or its blood supply. When properly positioned the device prevents further axial elongation of the eye. In alternative embodiments the band may be formed as a generally linear strap, a three legged or "Y" shaped strap or a four legged "X" shaped strap. A further alternative embodiment includes a circumferential band that is engagable with the legs of the posterior support band to secure the placement of the legs and to provide further support to the eye.

It is an advantage of the macular and scleral support device of the present invention that it provides improved posterior support to an eye globe.

It is another advantage of an embodiment of the macular and scleral support device of the present invention that it provides improved posterior eye support in three or more quadrants of the eye.

It is a further advantage of the macular and scleral support device of the present invention that it includes attachment legs having reinforced end portions that inhibit unwanted folding and buckling of the end portions at suture attachment points.

It is yet another advantage of the macular and scleral support device of the present invention that it is comprised of a mesh fabric that becomes engaged in position with the eye due to reactive scarring.

It is yet a further advantage of an embodiment of the macular and scleral support device of the present invention that it includes a circumferential band which is engagable to the leg portions of the posterior support band for providing secure positioning for the leg portions and enhanced eye globe support.

These and other objects and advantages of the present invention will no doubt become apparent to those skilled in the art upon reading the following detailed description which makes reference to the several figures of the drawings.

IN THE DRAWINGS

FIG. 1 is a top plan view of a first embodiment of the macular and scleral support device of the present invention;

FIG. 2 is a side elevational view of the support band depicted in FIG. 1;

FIG. 3 is a posterior view of the support band depicted in FIGS. 1 and 2 as applied to a right eye;

FIG. 4 is an anterior view of the device depicted in FIG. 3;

FIG. 5 is a posterior view depicting an alternative positional engagement of the support band from that which is depicted in FIG. 3;

FIG. 10 is a top plan view of a further embodiment of the macular and scleral support band of the present invention;

FIG. 11 is a posterior view of the support band of FIG. 10 as applied to a right eye;

FIG. 12 is an anterior view of the device depicted in FIG. 11;

DESCRIPTION OF THE PREFERRED EMBODIMENTS

Figure 6:
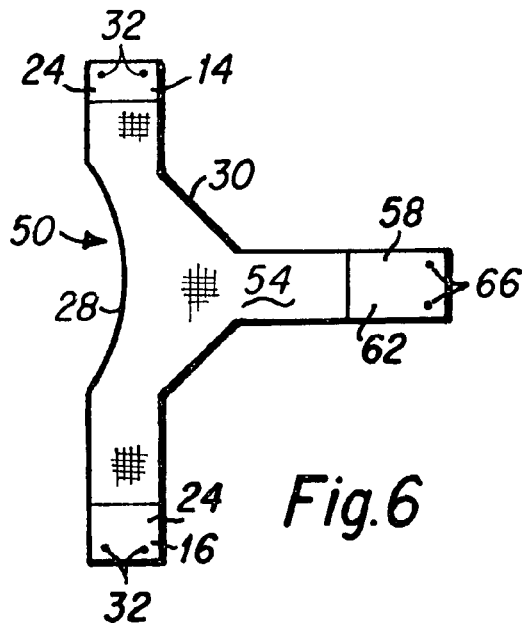
FIG. 6 is a top plan view of an alternative macular and scleral support band embodiment of the present invention.

Eyes with high axial myopia overgrow during the years in which the body is growing. Thus, in most cases, myopia is fairly stable following the cessation of corporeal growth, which occurs at about 17 years for a woman and 20 years for a man. In degenerative or progressive myopia, another factor is the presence of a weak collagen fiber in the tough scleral shell of the eye. The eye being a pressurized sphere, the thinned, posterior wall of the eye stretches, and so elongation of the eye may continue after the cessation of corporeal growth. The retina is progressively damaged by the continued stretching of the eye, resulting in degenerative changes which cause vision loss later in life. The accepted complications of this process involve retinal tears and detachments, premature cataract, and glaucoma, but most especially, macular degeneration. This latter problem causes uncorrectable vision loss later in life. The timing and severity of this loss is not easily predicted.

In the present invention, the applicant has developed a device which provides more extensive permanent positive mechanical external support to the parts of the eye globe most involved in the causation of the pathological changes of degenerative myopia. Generally, the flexible ocular restraint band of the present invention includes a thin flexible strap device that is made of a central woven, non-absorbable, surgical fabric, with a solid surgical quality material, such as (but not limited to) silicone rubber or a natural material at the strap ends. The combination allows a firm flexible but non-extensible device to be fashioned so as to provide a structural connection between the weak posterior pole of the eye and the thicker anterior scleral ring. While doing so, it is designed to also address the issue of equatorial growth and stretching. The device is sutured at its reinforced ends, with various degrees of tension, to the globe of the eye, and the reinforced ends prevent undesirable gathering, folds, pulls and creases of the fabric material. The creation of uneven pressure upon the outer surface of the eye is thus avoided. The surgical fabric, being porous, allows reactive scar tissue to enter its interstices, a process which may secure the implant and add to the mechanical bracing of the weak wall of the eye. Four alternative embodiments are described in detail herebelow, however the present invention is not to be limited thereto.

FIG. 1 is a top plan view depicting a first embodiment of the present invention and FIG. 2 is a side elevational view of the device depicted in FIG. 1. As depicted in FIGS. 1 and 2, the device 10 is generally formed as a strip of fabric material having a length L of approximately 70 millimeters and a width W of approximately 10 millimeters. These dimensions are deemed adequate for an adult eye, however the present invention is not to be limited to such dimensions as the object of the invention is that it be sutured to wrap behind the eye, and the eyes of different patients will have differing dimensions. The band 10 is preferably formed of a flexible material, such as a 1 mm Dacron surgical mesh fabric, and it includes end portions 14 and 16 and a central portion 20 between the end portions. One or both of the end portions 14 and 16 is bonded with a firm support material 24 that provides a flexible stiffness to the end portion of the band. In the preferred embodiment, the support material 24 at the end portions 14 and 16 is comprised of a silicone rubber that is heat bonded to the mesh fabric at the ends of the band. As is depicted in the side view of FIG. 2, the thickness of the support material 24 at the end portions 14 and 16 may be approximately 1.5 millimeters, where the thickness of the central mesh fabric 20 is approximately 1 millimeter.

The support material 24 may be bonded to varying lengths at the ends of the band to produce differing reactive scar tissue effects. That is, due to the location of particular eye muscle groups and the degree of reactive scar tissue desired, the length that the support material 24 may be bonded to the fabric mesh may vary from a minimum of approximately 5 mm (as depicted at end 14 of FIGS. 1 and 2) to a device where each support material portion 24 is approximately 25 mm or approximately one third of the length of the band 10, to a band in which the support material portion is bonded throughout the entire length of the band. Additionally, the device can be fabricated where the length of the support material 24 at a first end 14 differs from the length of the support material at the other end 16, as is depicted in FIGS. 1 and 2. It is to be understood that the present invention is not intended to be limited as to the nature of the materials (solid or woven) which are specified herein. That is, the device may be made from elements of natural material, and may be made from several materials that are laminated, cemented, fused, bonded, sewn or otherwise joined together.

As depicted in FIG. 1, it is not necessary that the band be formed with straight side edges, and the device 10 depicted in FIG. 1 preferably includes a central portion having curved side edges 28 and 30. The device having this curved side edge configuration, where one side edge 28 is concave and the other side edge 30 is convex, is advantageous in applying it to the patient's eye, in that it can be more readily sutured to the eye in an orientation around the optic nerve which protrudes from the posterior portion of the eye, as is described more fully with the aid of FIGS. 3 and 4. As has been indicated hereabove, the band is designed to be sutured to the anterior scleral portions of the eye and two suture attachment points 32 may be included, as are shown at each end 14 and 16 of the band within the support material 24. A significant feature of the present invention is that the support material 24 at the ends provides reinforcement to the mesh material at the ends, which prevents undesirable gathering, folding and pulling of the mesh material proximate the suture points, which will generally occur where the ends 14 and 16 lack the reinforcement provided by the support material 24.

FIGS. 3 and 4 depict the surgical attachment of the ocular support band 10 to a right eye globe, wherein FIG. 3 is a posterior depiction and FIG. 4 is an anterior depiction. As depicted in FIG. 3, the band 10 is placed around the posterior portion of the eye 36 such that the concave curve of side edge 28 curves around the optical nerve 37 that projects rearwardly from the eye 36. As will be understood by those skilled in the art, the band 10 is preferably implanted under the superior rectus muscle 38, over the insertion of the superior oblique muscle 39, medial to the lateral rectus muscle 40 and superior to the inferior rectus muscle 41. It is therefore positioned to provide posterior support to the eye between the optic nerve 37 and the insertion of the inferior oblique muscle 42. One sequence for surgical fixture to the eye is as follows.

The support arm for the superonasal location 43 is placed under the superior rectus muscle 38 and sutured to the globe of the anterior scleral ring (as depicted in FIG. 4). The arm to be placed inferonasally 44 is then passed over the insertion of the superior oblique muscle 39 anteriorally (nasal to the lateral rectus muscle 40) and then behind the insertion of the inferior oblique muscle 42 and superior to the inferior rectus muscle 41. During this passage twisting of the device 10 is prevented. The end in the inferornasal quadrant 44 is maneuvered to slip the central portion of the band over the posterior pole of the eye. It is then trimmed to length and sutured, with the desired tension to the scleral ring (as depicted in FIG. 4).

The curved side edge 28 aids in the positioning of the band 10 to avoid any contact with or pressure upon the optic nerve 44 and its blood supply, or any vortex veins that are identifiable. The band 10 may be sutured to the eye 40 with some tension, however the chief purpose of the band 10 is to prevent further rearward elongation of the eye, as a means to prevent further degeneration of the macular portion of the eye. The band 10 thus provides a posterior tensioned, support, in the fashion of a sling, sutured to the anterior globe in the superonasal and inferonasal quadrants at two suture points. It provides a new broad support to the posterior pole of the eye, as well as to the equatorial regions of two of the globe's four quadrants. It's materials have been well proven, by daily surgical use, to be un-degraded by long-term implantation in the body's tissues.

In some patients the band 10 may be advantageously placed in alternative locations in order to provide the desired support to the posterior pole of the, eye, and FIG. 5 is a posterior view (right eye) that is similar to FIG. 3 that depicts such an alternative band positioning. As depicted in FIG. 5, an upper support arm of the band 10 is positioned in the superonasal location 43 under the superior rectus muscle 38 and sutured to the globe at the anterior scleral ring. The band is then passed over the insertion of the superior oblique muscle 39 anteriorally (nasal to the lateral rectus muscle 40) and then behind or over the insertion of the inferior oblique muscle 42. The lower end is then passed into the inferotemporal quadrant 47. It is then trimmed to length and sutured, with the desired tension to the scleral ring. It is therefore to be understood that in FIG. 5 the device is positioned and sutured in the superonasal and inferotemporal quadrants at two suture points where the curved edge 28 is positioned such that the device avoids any contact with or pressure upon the optic nerve and its blood supply, and any vortex veins that are identified.

FIG. 6 is a top plan view that depicts a first alternative embodiment 50 of the present invention, which can be thought of as an enhanced band from that depicted in FIGS. 1 and 2 where a third leg 54 of the band is fabricated. In comparing the device 10 of FIG. 1 and the device 50 of FIG. 6, it is seen that the device of FIG. 6 is basically a "T" or "Y" shape having an integrally formed leg 54 that projects laterally from a side 30 of the band depicted in FIG. 1. The features and dimensions of the embodiment 50 depicted in FIG. 6 such as the length, width and thickness of the band are essentially the same as the band 10 depicted in FIGS. 1 and 2. The additional leg 54 may have a length of approximately 40 millimeters and it includes a reinforced end portion 58 comprising the support material 62 that is utilized with the ends 14 and 16 of the device 10. The end portion 62 of the additional leg may include suture points 66 within it such that it can be sutured to a further point along the anterior scleral ring of the eye.

Figure 7:
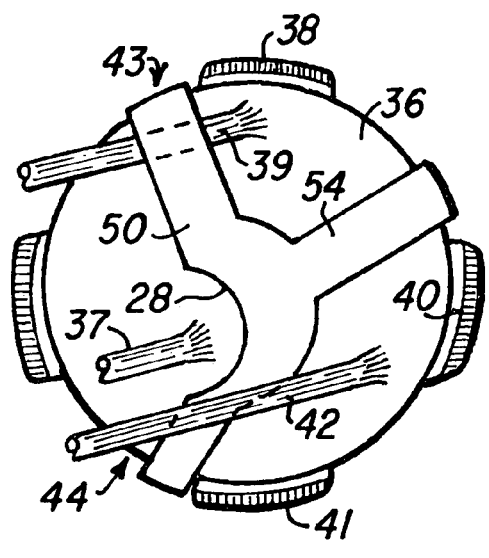
FIG. 7 is a posterior view of the support band of FIG. 6 as applied to a right eye.
Figure 8:
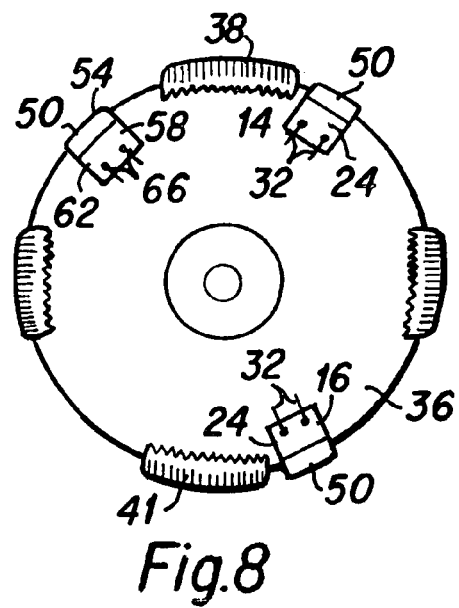
FIG. 8 is an anterior view of the device depicted in FIG. 7.

FIGS. 7 and 8 depict the surgical attachment of the ocular support band 50 to a right eye, wherein FIG. 7 is a posterior depiction and FIG. 8 is an anterior depiction. As depicted in FIG. 7, the band 50 is placed around the posterior portion of the eye 36 such that the concave curve of side edge 28 curves around the optical nerve 37 that projects rearwardly from the eye 36. As is seen in FIG. 8, the ends 14, 16 and 54 of the band 50 are wrapped towards the anterior portion of the eye, where sutures 32 are formed to join the support material portion 24 of the ends 14 and 16 to the scleral ring of the eye 36, and sutures 66 are used to join the leg 54 to the scleral ring. The leg 54 provides additional posterior support to the eye through the placement of the leg 54 within a third quadrant of the eye, and the curved edge 28 is preferably positioned to avoid any contact with or pressure upon the optic nerve and its blood supply, or any vortex veins that are identified. The band 50 may be sutured to the eye 40 with some tension, however the chief purpose of the band 50 is to prevent further rearward elongation of the eye, as a means to minimize or to prevent further degeneration of the macular portion of the eye.

The band 50 uses the same materials to provide a posterior support with three suture points, one being in each of three of the four quadrants of the globe of the eye. This form provides support to an even greater area of the portions of the globe which are involved in the over-growth and stretching of the eye found in cases of degenerative myopia. The legs of the band 50 may be advantageously engaged in differing eye quadrants for different patients, and, with reference to the discussion hereabove regarding the device 10 as depicted in FIGS. 3 and 5, the lower leg of the band 50 may be advantageously engaged in either the inferonasal quadrant or the inferotemporal quadrant of the eye globe. Similarly the leg 54 of band 50 may be engaged in either the superotemporal or the inferotemporal quadrants.

Figure 9:
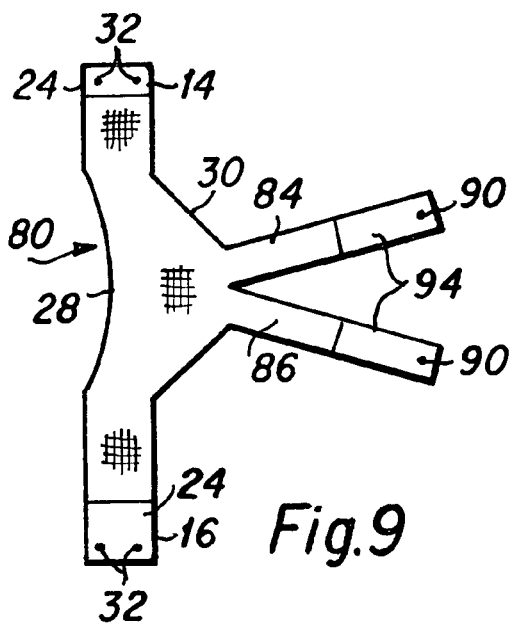
FIG. 9 is a top plan view of another embodiment of the macular and scleral support band of the present invention.

Yet another embodiment 80 of the present invention is depicted in a top plan view in FIG. 9. In comparing this embodiment 80 with the embodiment 50 depicted in FIG. 6, it is seen that this embodiment is formed as a band having four support legs 14, 16, 84 and 86, rather than the three legs 14, 16 and 54 depicted in FIG. 6. The device can generally be thought of as comprising the device 50 depicted in FIG. 6 where the additional leg 54 has been cut lengthwise to form two thinner separable legs 84 and 86, where each can have at least one suture point 90 formed in the support material 94 of the end portion of each leg. The length, width and thickness of the support material end portions 94 and mesh portions forming the device 80 are generally the same as those of the devices depicted in FIGS. 1–8. Arms 84 and 86 may be engaged in one or both of the temporal quadrants of the eye.

The embodiment 80 uses the same materials to provide a posterior support with four suture points, one being in each of the four quadrants of the globe of the eye. This form provides support to other selected portions of the globe which are identifiable as being involved in the over-growth and stretching of the eye found in cases of degenerative myopia.

FIG. 10 is a top plan view that depicts a further alternative embodiment 100 of the present invention, which can be thought of as an enhanced band from that depicted in FIG. 6, where a fourth leg of the band is fabricated. In comparing the device 100 of FIG. 10 with the previously described devices, it is seen that the device 100 is basically an "X" shape having a central portion 104 and four integrally formed legs 108, 112, 116 and 120. The features and dimensions of the embodiment 100 depicted in FIG. 10, such as the length, width and thickness of the band are essentially the same as the band 10 depicted in FIGS. 1 and 2. Each leg may have a length of approximately 40 mm, including a reinforced end portion 124 comprising the support material 62 that is utilized with the ends 14 and 16 of the device 10. Each end portion 124 may include suture points 128 such that it can be sutured to a desired location along the anterior scleral ring of the eye. As with the support band embodiments depicted hereabove, the device 100 preferably includes a concave curved side edge 132 of the body portion 104 that corresponds to the curved side edge 28 of the prior embodiments. Attachment provides support to all four of the eye's quadrants.

FIGS. 11 and 12 depict the surgical attachment of the ocular support band 100 to a right eye, wherein FIG. 11 is a posterior depiction and FIG. 12 is an anterior depiction. As depicted in FIG. 11, the band 100 is placed around the posterior portion of the eye 36 such that the concave curve of side edge 132 curves around the optical nerve 37 that projects rearwardly from the eye 36. As is seen in FIG. 12, the ends 124 of the legs 108, 112, 116 and 120 are wrapped towards the anterior portion of the eye, where sutures 140 are formed to join the support material portion 124 of the legs to the scleral ring of the eye 36. Each one of the legs is placed within a quadrant of the eye, and the curved edge 132 is preferably positioned to avoid any contact with or pressure upon the optic nerve and its blood supply, or any vortex veins that are identified. The band 100 may be sutured to the eye with some tension, however the chief purpose of the band 100 is to prevent further rearward elongation of the eye, as a means to prevent further degeneration of the macular portion of the eye. The band 100 uses the same materials as the embodiments described above to provide a posterior support with four suture points. This form provides further support to an even greater area of the portions of the globe which are involved in the over-growth and stretching of the eye found in case of degenerative myopia.

Figure 13:
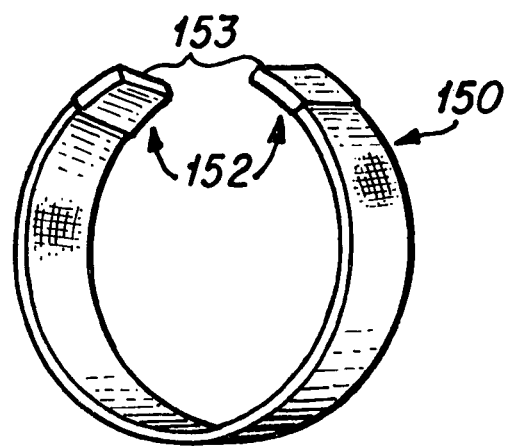
FIG. 13 is a perspective view of a circumferential support band that is included within an alternative embodiment of the macular and scleral support device of the present invention.
Figure 14:
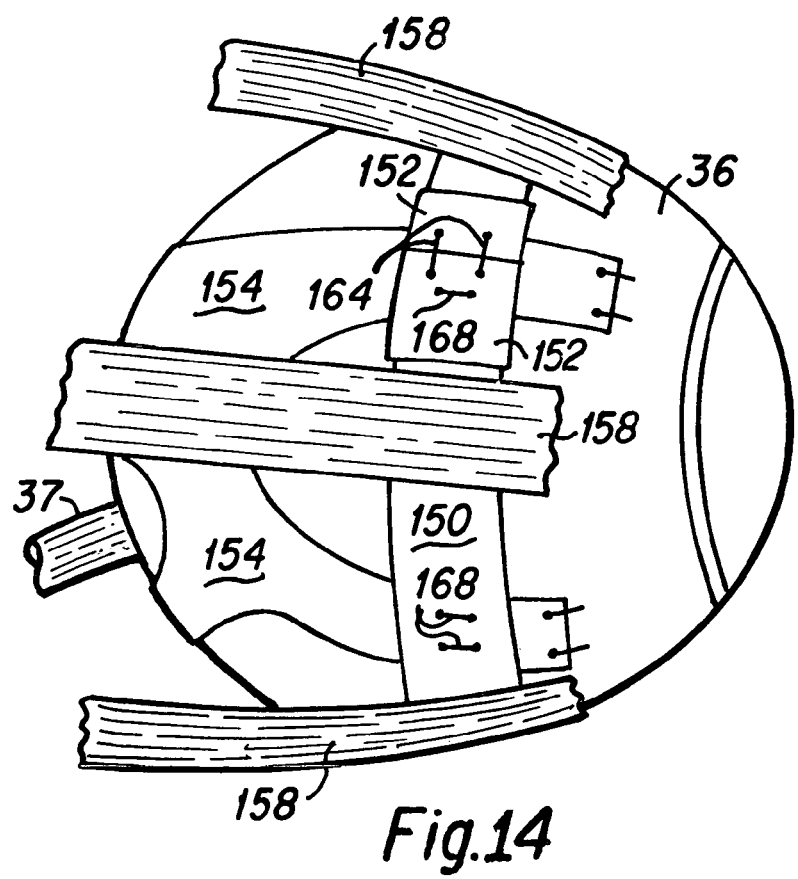
FIG. 14 is a side elevational view of an alternative macular and scleral support device of the present invention including a circumferential band that is engagable with a posterior support band.

An alternative embodiment of a macular and scleral support device of the present invention is depicted in FIGS. 13 and 14, wherein FIG. 13 is a perspective view of a circumferential support band that is engagable with a posterior support band described hereabove, and FIG. 14 is a side elevational view of a right eye globe having a circumferential and posterior support band engaged thereto. As depicted in FIG. 13, the circumferential band is generally rectangular and typically has a length of approximately 100 millimeters and a width of approximately 5–25 millimeters and is comprised of the same materials as the posterior support bands described hereabove. The ends 152 of the circumferential band 150 are preferably, though not necessarily, reinforced with a firm support material 153 (such as has been described hereabove with regard to the posterior support bands) that provides a flexible stiffness to the end portions of the circumferential band 150, and acts to prevent folding and pulling of the mesh material proximate suture points at the ends of the band 150.

As depicted in FIG. 14, the circumferential band 150 is placed around the equator of the eye globe 36 to provide further support for the eye alone or in combination with a posterior support band 154, such as any of the bands 10, 50, 80 and 100 described hereabove. The band 150 is located anterior to the insertion of the superior and inferior oblique muscles (not shown), and is placed under each of the four rectus muscles 158. The band 150 is preferably installed following the engagement of the posterior support band 154 as described above, although it may alternatively be prepositioned before installation of the posterior support band. The ends 152 of the circumferential band 150 are joined together with sutures 164, and the circumferential band 150 is preferably engaged by sutures 168 to the legs of the posterior support band 154 where there is a crossing of the circumferential band with the legs of the posterior support band. The suturing 168 of the legs of the posterior support band 154 to the circumferential band 150 acts to secure the placement of the legs and prevent future movement of the posterior support band and the circumferential band. The circumferential band also provides equatorial support to the eye globe. When placed in otherwise unsupported quadrants of the eye, the band is to be positioned with episcleral sutures of non-absorbable material.

The device of the present invention appears to be quite effective in adult eyes. While it does reinforce the thin, stretched sclera, it does not materially shorten the eye, nor does it reduce future macular complications from the existing length of the eye. The basic concept of the invention is a mechanical solution to what is basically a mechanical problem for eyes of 27 mm length, or greater. The goal is to prevent further stretching which would cause even more progressive damage later in life. Further enhancements of the present invention are contemplated wherein chemical or physical agents are incorporated within the fabric of the band to either retard or stimulate the growth of scarring tissue in or on the weak natural sclera of the eye. The present invention should be considered at almost any patient age if the eye exceeds 27 mm in length and risk of future myopic macular degeneration is significant. Additionally, if the intraocular pressure is over approximately 16 mm Hg, pressure reducing drops should be administered to keep the pressure in the lower teens. This is, after all, the force which stretches the eye further.

While the present invention has been shown and described with regard to certain preferred embodiments, it is to be understood that modifications in form and detail will no doubt be developed by those skilled in the art upon reviewing this disclosure. It is therefore intended that the following claims cover all such alterations and modifications that nevertheless include the true spirit and scope of the inventive features of the present invention.

I claim:

1. A macular and scleral support device, comprising:
 a strip of material including a central portion and at least two end portions that are integrally formed with said central portion;
 each said end portion being reinforced with a portion of support material joined thereto and are adapted for sutured engagement with an anterior portion of an eye globe; and
 wherein a length of said support material at one said end portion is greater than a length of said support material that is joined to another said end portion.

2. A macular and scleral support device as described in claim 1 wherein said strip of material is formed with three said end portions.

3. A macular and scleral support device as described in claim 2, wherein said strip of material is generally "T" shaped.

4. A macular and scleral support device as described in claim 7 wherein said "T" shaped material includes a top portion and a leg portion, and wherein said top portion is formed with a concave curve edge thereof.

5. A macular and scleral support device as described in claim 2, wherein said strip of material is generally "Y" shaped.

6. A macular and scleral support device as described in claim 1 wherein said strip of material is formed with four said end portions.

7. A macular and scleral support device as described in claim 6 wherein said strip of material is generally "X" shaped.

8. A macular and scleral support device as described in claim 7 wherein said strip of material is formed with a body portion and four legs that are integrally formed therewith, and wherein said body portion includes a concave curved side edge that is disposed between two of said legs.

9. A macular and scleral support device as described in claim 1 wherein said support material is comprised of silicone rubber or other man made or natural material.

10. A macular and scleral support device as described in claim 1 wherein said strip of material is comprised of a fabric mesh material.

11. A macular and scleral support device as described in claim 10 wherein said fabric mesh material is comprised of Dacron.

12. A macular and scleral support device as described in claim 1 wherein said support material is joined to an approximately 5 mm to 25 mm length of each said end portion.

13. A macular and scleral support device as described in claim 1 wherein said strip of material is formed with two side edges and two end edges.

14. A macular and scleral support device as described in claim 13 wherein said side edges are approximately 70 mm long and said end edges are approximately 5–25 mm long.

15. A macular and scleral support device as described in claim 13 wherein a portion of at least one of said side edges is curved.

16. A macular and scleral support device as described in claim 15, wherein both of said two side edges include curved portions, and wherein one of said side edges is formed with a concave curve and the other of said side edges is formed with a convex curve.

17. A macular and scleral support device as described in claim 1, further including a second strip of material that is adapted for engagement with said strip of material at locations between said central portion and said end portions of said strip of material.

18. A macular and scleral support device as described in claim 17 wherein said second strip of material is formed with a length of approximately 100 millimeters and a width of approximately 5–25 millimeters.

19. A macular and scleral support device as described in claim 1 wherein said first strip of material is formed with three said end portions, wherein one said end portion is adapted for engagement within a superonasal quadrant of said eye globe, another said end portion is adapted for engagement within a inferonasal quadrant of said eye globe, and a third end portion is adapted for engagement within a superotemporal quadrant of said eye globe.

20. A macular and scleral support device as described in claim 1, wherein a second strip of material is adapted for circumferential engagement around an equatorial portion of said eye globe, and wherein said second strip of material is adapted for sutured engagement with said first strip of material at locations between said central portion and said end portions of said first strip of material.

21. A macular and scleral support device, comprising:

a strip of material including a central portion that is adapted for placement over a posterior portion of an eye globe for providing support thereto;

at least two end portions of said strip of material that are integrally formed with said central portion and adapted for sutured engagement with an anterior portion of said eye globe;

and wherein said strip of material is formed with two side edges and two end edges, and wherein both of said two side edges include two straight portions and a curved portion disposed therebetween, and wherein one of said side edges is formed with a concave curve and the other of said side edges is formed with a convex curve.

22. A macular and scleral support device as described in claim 21 wherein said strip of material is comprised of a natural material.

23. A macular and scleral support device as described in claim 21 wherein said strip of material is comprised of a fabric mesh material.

24. A macular and scleral support device as described in claim 23 wherein said fabric mesh material is comprised of Dacron.

25. A macular and scleral support device as described in claim 21 wherein each said end portion is reinforced with a portion of support material joined thereto, and wherein said support material is comprised of silicone rubber or other man made or natural material.

26. A macular and scleral support device as described in claim 25 wherein said support material is joined to an approximately 5 mm to 25 mm length of each said end portion.

27. A macular and scleral support device as described in claim 25 wherein said support material is joined to each said end portion, and where a length of said support material at one said end portion is greater than a length of said support material that is joined to another said end portion.

* * * * *